United States Patent [19]

Butts et al.

[11] 4,435,605

[45] Mar. 6, 1984

[54] PROCESS FOR PREPARATION OF 2-PHENYLETHYL ALCOHOLS FROM AROMATIC ALDEHYDES

[75] Inventors: Susan B. Butts; George E. Hartwell, both of Midland, Mich.

[73] Assignee: The Dow Chemical Company, Midland, Mich.

[21] Appl. No.: 412,333

[22] Filed: Aug. 27, 1982

[51] Int. Cl.³ ............................................. C07C 27/22
[52] U.S. Cl. ................................. 568/878; 568/705; 568/715; 568/812; 568/876; 568/882
[58] Field of Search ............... 568/715, 705, 812, 878, 568/882, 909, 881, 876

[56] References Cited

U.S. PATENT DOCUMENTS

| | | | |
|---|---|---|---|
| 1,591,125 | 7/1926 | Harlow et al. | 568/715 |
| 1,802,466 | 4/1931 | Ho | 568/880 |
| 2,638,488 | 5/1953 | Cerveny | 568/882 |
| 2,658,083 | 11/1953 | Burney et al. | 568/882 |
| 3,159,679 | 12/1964 | Kyle et al. | 568/909 |
| 3,248,432 | 4/1966 | Riley et al. | 568/882 |
| 3,285,948 | 11/1966 | Butter | 568/890 |
| 3,867,430 | 2/1975 | Grozhan et al. | 568/715 |
| 4,072,720 | 2/1978 | Haag et al. | 568/882 |
| 4,130,574 | 12/1978 | Fry | 568/881 |
| 4,158,100 | 6/1979 | Sherwin et al. | 568/715 |
| 4,291,179 | 9/1981 | Goetz et al. | 568/882 |

FOREIGN PATENT DOCUMENTS

| | | | |
|---|---|---|---|
| 648822 | 7/1959 | Canada | 568/715 |
| 53-21131 | 2/1978 | Japan | 568/715 |
| 57-26634 | 2/1982 | Japan | 568/715 |
| 948676 | 2/1964 | United Kingdom | 568/715 |
| 951506 | 3/1964 | United Kingdom | 568/882 |
| 1183537 | 3/1970 | United Kingdom | 568/715 |

OTHER PUBLICATIONS

Wender et al., "J. Amer. Chem. Soc.", vol. 74, (1949), pp. 4160–4161.
Kryukov et al., "Neftekhimiya", vol. 10(1), p. 83, (1970).
Butter "Chemical Abstract", vol. 59p, 2648a.
Orhhin "Advances in Catalysis," vol. V, pp. 383–414, (1953).

Primary Examiner—Werren B. Lone
Attorney, Agent, or Firm—Norman L. Sims

[57] ABSTRACT

The invention is a process for the preparation of a 2-phenylethyl alcohol which comprises contacting an aromatic aldehyde with carbon monoxide and hydrogen in a solvent comprising an oxygenated polar hydrocarbon and water, in the presence of a catalytic amount of a catalyst comprising a cobalt compound, a ruthenium salt and an iodine salt, at elevated temperatures and a pressure of between 600 and 45,000 psi.

7 Claims, No Drawings

PROCESS FOR PREPARATION OF 2-PHENYLETHYL ALCOHOLS FROM AROMATIC ALDEHYDES

BACKGROUND OF THE INVENTION

This invention relates to the preparation of 2-phenylethyl alcohols. More specifically it relates to the preparation of 2-phenylethyl alcohols from aromatic aldehydes.

It has long been desirable to prepare 2-phenylethyl alcohol in a low cost process. This material is a valuable intermediate in the preparation of fragrances and of styrene, a commercial chemical with widely varying uses. In the past, it has been proposed that 2-phenylethyl alcohol be prepared from benzyl alcohol. For example, the reaction has been described by Wender, I. et al., *J. Amer. Chem. Soc.*, 71 (1949), pages 4160–4161 wherein the use of a cobalt catalyst was described. This early work is summarized by Orchin in *Advances in Catalysis*, Vol. V (1953), pages 393–414. This auther reports that, at 183° C., a 50–60 percent yield of toluene and a 23–35 percent yield of 2-phenylethyl alcohol is obtained. Other workers have experimented with this reaction, particularly Y. B. Kryukov et al., Neftekhimiya, 1970, 10 (1), at page 83. Here, a vapor phase reaction is described over an iron, alumina, vanadium and potassium catalyst at 430° C. and 50 atmospheres pressure. Unfortunately, in this latter reaction extremely low selectivities to the 2-phenylethyl alcohol were obtained.

Though not related to the formation of 2-phenylethyl alcohol, homologation has been described by a series of patents assigned to Commercial Solvents, including U.S. Pat. Nos. 3,248,432 and 3,285,948, British Patent 951,506, and Belgian Pat. Nos. 618,413 and 625,939. These references are primarily concerned with the homologation of methanol to form ethanol. The catalyst system shown in U.S. Pat. No. 3,285,948 is of particular interest. This patent discloses the use of a cobalt catalyst promoted with a ruthenium or osmium halide and iodine. The patent also discloses the optional use of from 0.1 to 20 percent of water based on the methanol charged in the reaction system. Reaction temperatures indicated are 175° C. to 230° C., preferably from 190° C. to 210° C.

Unfortunately, the foregoing references fail to result in the preparation of high yields of 2-phenylethyl alcohol. The work reported by Orchin forms so little 2-phenylethyl alcohol that such reaction could not be considered of commercial importance.

Sherwin et al., U.S. Pat. No. 4,158,100 teach that 2-phenylethyl alcohol may be prepared from benzyl alcohol by homologation with hydrogen and carbon monoxide in the presence of a cobalt catalyst promoted with ruthenium and iodine compounds, in the presence of water at a temperature from 100° C. to 165° C.

The present invention gives surprisingly higher yields of the desired 2-phenylethyl alcohols than homologation of benzyl alcohols. These surprising yields are the result of the discovery that 2-phenylethyl alcohol can be prepared from aromatic aldehydes. It has been further discovered that the yields are increased by the use of certain solvents.

SUMMARY OF THE INVENTION

The invention is a process for the preparation of a 2-phenylethyl alcohol which comprises contacting an aromatic aldehyde with carbon monoxide and hydrogen in a solvent comprising an oxygenated polar hydrocarbon and water, in the presence of a catalytic amount of a catalyst comprising a cobalt compound, a ruthenium salt and an iodine salt, at elevated temperatures and a pressure of between about 600 and 45,000 psi, wherein the aromatic aldehyde is represented by the formula

and the 2-phenylethyl alcohol is represented by the formula

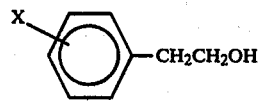

wherein X is a hydrogen, halogen, alkyl, alkoxy or nitro group.

DETAILED DESCRIPTION OF THE INVENTION

In this invention, substituted and unsubstituted 2-phenylethyl alcohols are prepared from substituted and unsubstituted aromatic aldehydes. The substituents, represented above by X, are preferably alkyl and most preferably methyl. Further, it is preferable that the substituent be in the para position as the rate of reaction for the para-substituted aromatic aldehydes is faster than the ortho or meta species.

It has been discovered that the use of aromatic aldehydes in place of benzyl alcohols to prepare 2-phenylethyl alcohol gives a higher yield of the desired products.

It has been further discovered that the yields and selectivities for the 2-phenylethyl alcohol are surprisingly increased by the use of certain solvents. The main component of the solvent is an oxygenated polar hydrocarbon such as, for example, tetrahydrofuran, acetone, dioxane, or a $C_2$ to $C_4$ lower alcohol; preferred are tetrahydrofuran, acetone or dioxane; and most preferred is tetrahydrofuran.

These oxygenated polar hydrocarbons are mixed with water wherein the amount of water is between about 0.1 and 15 weight percent by weight of the aromatic aldehyde, preferably 10 to 15 weight percent. The oxygenated polar hydrocarbon is preferably water-miscible. Some components of the catalyst are water-soluble so that if a separate water phase is formed, the catalyst will be extracted from the organic reaction phase. The use of the oxygenated polar hydrocarbon component of the solvent improves the selectivity and yield of this reaction. An amount of solvent to dissolve catalyst and reactants is sufficient.

The catalyst system comprises a cobalt compound promoted by ruthenium and iodide. The cobalt catalysts used in the present invention may be present in between about 0.25 and 5.0 mole percent of cobalt per mole of benzaldehyde. Over this range, variations in the amount of catalyst are not particularly critical. As a practical matter, from 1.0 to 5.0 mole percent is employed. The cobalt catalyst added to the system is selected so as to be soluble in the reaction medium. This cobalt catalyst can be formed in situ by adding to the system an organic salt of cobalt, particularly a water-soluble compound. Suitable organic salts of cobalt include, cobalt acetate, cobalt formate or cobalt prionate. Such materials are readily converted to the active cobalt form during the reaction.

The promoters employed, i.e., the ruthenium and the iodide salts, are used in combination. The ruthenium salt is most desirably added as the halide, and between about 0.02 and 0.30 mole of ruthenium should be present for each mole of cobalt, preferably between about 0.04 and 0.15 moles. In the case of the iodide salt, this may be formed by adding elemental iodine to the reaction system or by introducing a salt form of the iodide, such as an alkali metal iodide. Generally, between about 0.03 and 2.0 moles of iodide per mole of cobalt should be present, preferably from between about 0.10 and 1.0.

The amount of hydrogen and carbon monoxide added is generally in stoichiometric excess of the amount of aromatic aldehyde used. As a minimum, at least stoichiometric quantities must be added and excesses up to 20 times the stoichiometric amount are useful. Inert gases such as nitrogen may also be present in the reaction mixture if desired.

The advantages of the present invention may be obtained over a wide range of hydrogen to carbon monoxide ratios. As little as one-half mole of hydrogen to each mole of carbon monoxide may be used, and up to 5 moles of hydrogen to one mole of carbon monoxide may be used. The most preferred range is from 3:1 to 1:1. Sufficient carbon monoxide must be present to maintain the cobalt catalyst in its active state.

The process should be run at elevated temperatures. Suitable temperatures are between about 115° C. and 145° C. Below 115° C. the reaction rate is too slow and above 145° C., the dominant reaction is the reduction of the aldehyde to a methyl group.

Elevated pressures are required for this process. Suitable pressures are between about 590 and 45,000 psi. Preferable pressures are between about 1000 and 5000 psi, most preferably between about 3000 and 5000. Increased pressures tend to favor selectivity to the 2-phenylethyl alcohol. However, the use of higher pressures is limited by practical considerations such as the selection of equipment and safety factors.

The reaction period is not critical, but should be selected so as to achieve acceptable conversions without unduly lengthening the process cycles. As a practical matter, the reaction period would range from 2 to 5 hours.

The aromatic aldehydes used herein may be mixed with other organic compounds, so long as such compounds do not interfere with the reaction.

SPECIFIC EMBODIMENTS

The following examples are included to further illustrate the invention and are not intended to limit the scope of the invention as described and claimed herein.

EXAMPLE 1

The following materials were combined, in the order shown, in a glass liner under an atmosphere of nitrogen; sodium iodide (0.395 mmole), $Co_2(CO)_8$ (0.8 mmole), ruthenium chloride (0.2 mmole), p-tolualdehyde (31.0 mmole), tetrahydrofuran (3.6 ml) and water (0.5 ml). The liner was sealed in a 180 cc rocking autoclave and pressurized with 1700 psig of carbon monoxide and 1700 psig of hydrogen. The reactor was heated, with rocking agitation, up to 135° C. and maintained at 135° C. for 2.75 hours, and thereafter allowed to cool. Gas chromatographic analysis of the product indicated 99 percent conversion of the p-tolualdehyde and the formation of the following products; p-methyl-2-phenethyl alcohol (63.6 percent), p-xylene (15.1 percent), ethers (9.5 percent) and p-methyl benzyl alcohol (5.3 percent).

EXAMPLE 2

The following materials were combined, in the order shown, in a glass liner under an atmosphere of nitrogen; sodium iodide (0.44 mmole), $Co_2(CO)_8$ (0.79 mmole), ruthenium chloride (0.2 mmole), p-tolualdehyde (31 mmole), dioxane (3.6 ml) and water (0.5 ml). The liner was sealed in a 180 cc rocking autoclave and pressurized with 1700 psig of carbon monoxide and 1700 psig of hydrogen. The reactor was heated to 140° C., with rocking agitation, and thereafter maintained at 140° C. for 2.75 hours, and then allowed to cool. Gas chromatographic analysis of the product indicates over 99 percent conversion of the p-tolualdehyde and the formation of the following products; p-methyl-2-phenethyl alcohol (47.8 percent), p-xylene (15.1 percent), ethers (15.0 percent) and p-methyl benzyl alcohol (21.1 percent).

EXAMPLE 3

The following materials were combined, in the order shown, in a glass liner under an atmosphere of nitrogen; sodium iodide (0.33 mmole), $Co_2(CO)_8$ (0.79 mmole), ruthenium chloride (0.2 mmole), p-tolualdehyde (30 mmole), acetone (3.5 ml) and water (0.5 ml). The liner was sealed in a 180 cc rocking autoclave and pressurized with 1700 psig of carbon monoxide and 1700 psig of hydrogen. The reactor was heated to 140° C., with rocking agitation, and thereafter maintained at 140° C. for 3.75 hours, and then cooled. Gas chromatography analysis of the product indicates over 99 percent conversion of the p-tolualdehyde and the formation of the following products; p-methyl-2-phenethyl alcohol (54.8 percent), p-xylene (14.1 percent), ethers (13.2 percent) and p-methyl benzyl alcohol (7.4 percent).

EXAMPLE 4

The following materials were combined, in the order shown, in a glass liner under an atmosphere of nitrogen; sodium iodide (0.016 g), $Co_2(CO)_8$ (0.090 g), ruthenium chloride (0.016 g), p-methyl benzyl alcohol (0.97 g), acetone (1.2 ml) and water (0.17 ml). The liner was sealed in a 180 cc rocking autoclave and pressurized with 3400 psig of a 1:1 mixture of carbon monoxide and hydrogen. The reactor was heated, with rocking agitation, for 4.0 hours at 135° C. The gas chromatographic analysis of the product is compiled in Table I.

EXAMPL 5

The following materials were combined, in the order shown, in a glass liner under an atmosphere of nitrogen; sodium iodide (0.05 g), $Co_2(CO)_8$ (0.27 g), ruthenium chloride (0.05 g), p-tolualdehyde (3.5 g), acetone (3.4 ml) and water (0.50 ml). The liner was sealed in a 180 cc rocking autoclave and pressurized with 3450 psig of a 1:1 mixture of carbon monoxide and hydrogen. The reactor was heated to 135° C. with rocking agitation and maintained at 135° C. for 3.25 hours and allowed to cool. Results of gas chromatographic analysis of the product are compiled in Table I.

TABLE I

| Example | Starting Reactant | Products (mole %) | | | | |
|---|---|---|---|---|---|---|
| | | Xylene | p-Tolualdehyde | p-Methyl Benzyl Alcohol | Ethers | p-Methyl 2-phenylethyl Alcohol |
| 4 | p-methyl benzyl alcohol | 32.3 | — | 1.8 | 18.5 | 38.0 |
| 5 | p-tolualdehyde | 23.5 | 0.4 | 4.9 | 11.2 | 54.0 |

Table I demonstrates that a significantly higher yield of 2-phenylethyl alcohol is achieved where p-tolualdehyde is the starting reactant than when p-methyl benzyl alcohol is the starting reactant.

What is claimed is:

1. A process for the preparation of a 2-phenylethyl alcohol which comprises contacting a aromatic aldehyde with carbon monoxide and hydrogen in a solvent comprising an oxygenated polar hydrocarbon and water, in the presence of a catalytic amount of a catalyst comprising a cobalt compound, a ruthenium salt and an iodine salt, at elevated temperatures and a pressure of between about 600 and 45,000 psi, wherein the aromatic aldehyde is represented by the formula

I and the 2-phenylethyl alcohol is represented by the formula

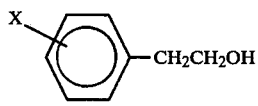

II wherein X is a hydrogen, halogen, alkyl, alkoxy or nitro group.

2. The process of claim 1 wherein X is alkyl.
3. The process of claim 2 wherein X is methyl.
4. The process of claim 1 wherein X is in the para position.
5. The process of claim 1 wherein the oxygenated polar hydrocarbon solvent is acetone, tetrahydrofuran, dioxane or a $C_2$ to $C_4$ lower alcohol.
6. The process of claim 5 wherein the oxygenated polar hydrocarbon solvent is tetrahydrofuran.
7. The process of claim 1 wherein the temperature is between about 115° C. and 145° C.

* * * * *